(12) United States Patent
McErlean et al.

(10) Patent No.: US 11,497,926 B2
(45) Date of Patent: Nov. 15, 2022

(54) METHOD AND APPARATUS FOR THE TREATMENT, MANAGEMENT AND/OR CONTROL OF PAIN

(71) Applicant: EMBLATION LIMITED, Alloa (GB)

(72) Inventors: Eamon McErlean, Alloa (GB); Gary Beale, Alloa (GB)

(73) Assignee: EMBLATION LIMITED, Alloa (GB)

( * ) Notice: Subject to any disclaimer, the term of this patent is extended or adjusted under 35 U.S.C. 154(b) by 185 days.

(21) Appl. No.: 15/230,808

(22) Filed: Aug. 8, 2016

(65) Prior Publication Data

US 2018/0036551 A1 Feb. 8, 2018

(51) Int. Cl.
*A61N 5/02* (2006.01)

(52) U.S. Cl.
CPC .................................. *A61N 5/022* (2013.01)

(58) Field of Classification Search
CPC .. A61N 5/02; A61N 5/022; A61B 2018/1861; A61B 2018/1869; A61B 2017/00774; A61B 2017/00747; A61B 17/12; A61P 17/12
See application file for complete search history.

(56) References Cited

U.S. PATENT DOCUMENTS

| 4,149,170 | A | 4/1979 | Campbell et al. |
|---|---|---|---|
| 4,517,975 | A | 5/1985 | Garito et al. |
| 5,091,707 | A | 2/1992 | Wollmerschauser et al. |
| 5,195,965 | A | 3/1993 | Shantha |
| 5,272,301 | A | 12/1993 | Finger et al. |
| 5,507,791 | A * | 4/1996 | Sit'ko ...................... A61N 5/02 128/898 |
| 5,649,973 | A * | 7/1997 | Tierney .................. A61B 18/18 607/101 |
| 5,683,386 | A | 11/1997 | Ellman et al. |
| 5,879,379 | A * | 3/1999 | Mason ...................... A61F 7/10 607/108 |
| 5,993,480 | A * | 11/1999 | Burrows ................... A61F 7/02 607/112 |
| 6,047,216 | A | 4/2000 | Carl et al. |
| 6,104,959 | A | 8/2000 | Spertell |
| 6,710,673 | B1 | 3/2004 | Jokerst |
| 7,052,283 | B2 | 5/2006 | Pixley et al. |

(Continued)

FOREIGN PATENT DOCUMENTS

| CN | 1277879 | 12/2000 |
|---|---|---|
| EP | 2485326 | 8/2012 |

(Continued)

OTHER PUBLICATIONS

Bevans, J.S. 'A comparison of electrosurgery and sharp debridement in the treatment of chronic neurovascular, neurofibrous and hard corns', The Foot, Mar. 11, 2010, vol. 20, Issue 1, pp. 12-17. [online] [retrieved on Sep. 27, 2018. Internet <URL: https://www.sciencedirect.com/science/article/pii/S0958259210000040?via%3Dihub>.*

(Continued)

*Primary Examiner* — Linda C Dvorak
*Assistant Examiner* — Annabeth E Rodriguez
(74) *Attorney, Agent, or Firm* — Sheridan Ross P.C.

(57) ABSTRACT

Methods and apparatus for the treatment, management and/or control of pain, in particular pain associated with, or caused or contributed to by, certain dermatological conditions.

20 Claims, 2 Drawing Sheets

(56) References Cited

U.S. PATENT DOCUMENTS

Figure 1A:
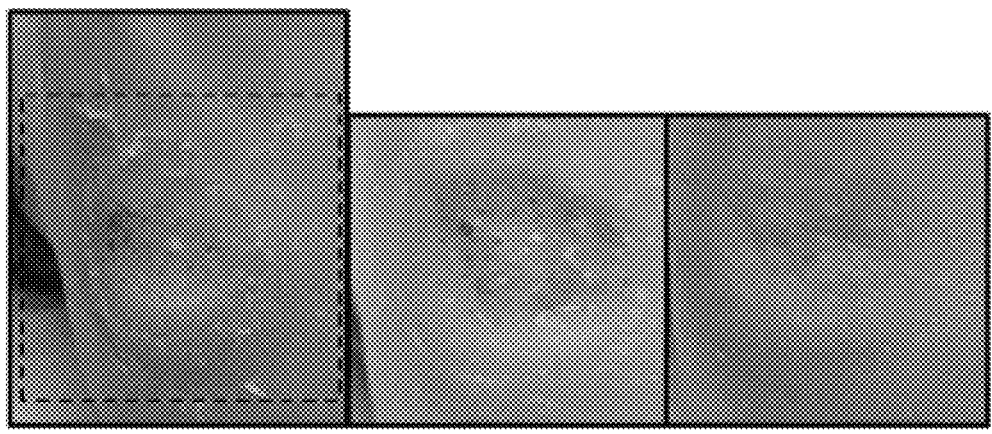

| | | | |
|---|---|---|---|
| 7,211,411 B2 | 5/2007 | Neefe et al. | |
| 7,292,893 B2 | 11/2007 | Hoenig et al. | |
| 7,981,112 B1* | 7/2011 | Neev | A61B 18/08 606/27 |
| 9,498,284 B2 | 11/2016 | McErlean et al. | |
| 9,543,061 B2 | 1/2017 | McErlean et al. | |
| 2001/0050605 A1 | 12/2001 | Suggiura et al. | |
| 2003/0012830 A1* | 1/2003 | Small | A61K 9/0014 424/727 |
| 2003/0225441 A1 | 12/2003 | Boynton et al. | |
| 2005/0251231 A1 | 11/2005 | Goldberg | |
| 2006/0020312 A1 | 1/2006 | Eggers et al. | |
| 2006/0235286 A1 | 10/2006 | Stone et al. | |
| 2006/0265034 A1* | 11/2006 | Aknine | A61B 18/1815 607/101 |
| 2008/0149100 A1 | 6/2008 | Van Holst et al. | |
| 2008/0183164 A1* | 7/2008 | Elkins | A61B 18/02 606/21 |
| 2008/0294073 A1* | 11/2008 | Barthe | A61N 7/02 601/3 |
| 2008/0319517 A1 | 12/2008 | Cumbie | |
| 2010/0010480 A1* | 1/2010 | Mehta | A61B 18/14 606/9 |
| 2010/0114086 A1* | 5/2010 | Deem | A61N 5/025 606/33 |
| 2010/0211059 A1* | 8/2010 | Deem | A61B 18/1815 606/33 |
| 2012/0016356 A1* | 1/2012 | Beale | A61N 5/025 606/33 |
| 2012/0203218 A1 | 8/2012 | Bonn | |
| 2013/0190750 A1 | 7/2013 | Behnke et al. | |
| 2013/0282084 A1 | 10/2013 | Mathur et al. | |
| 2014/0066837 A1* | 3/2014 | Moy | A61K 38/18 604/22 |
| 2014/0249601 A1* | 9/2014 | Bachinski | A61N 1/0492 607/59 |
| 2015/0080875 A1 | 3/2015 | Kasprzyk et al. | |
| 2016/0324577 A1 | 11/2016 | Beale et al. | |
| 2017/0056106 A1 | 3/2017 | McErlean et al. | |
| 2018/0280715 A1 | 10/2018 | McErlean et al. | |
| 2019/0069949 A1 | 3/2019 | Vrba et al. | |
| 2019/0255348 A1 | 8/2019 | Beale et al. | |
| 2019/0274758 A1 | 9/2019 | Beale et al. | |
| 2020/0353278 A1 | 11/2020 | McErlean et al. | |

FOREIGN PATENT DOCUMENTS

| | | |
|---|---|---|
| WO | WO 91/03207 | 3/1991 |
| WO | WO 93/22977 | 11/1993 |
| WO | WO 98/49933 | 11/1998 |

OTHER PUBLICATIONS

Koltaj, S. 'Er:YAG Laser Treatment of Intractable Plantar Keratosis (IPK)', Journal of the Laser and Health Academy, May 2013, vol. 2013, No. 1, pp. 32-35. [online] [retrieved on Sep. 27, 2018]. Internet <URL: https://www.laserandhealthacademy.com/media/objave/academy/priponke/32_35_koltaj_intractable_plantar_keratosis_jl.*

Cavaliere, Raymond G. 'Treatment of Porokeratosis Plantaris Discreta', The Podiatry Institute, 1993, pp. 145-149. (Predilection and Clinical Assessment) [retrieved on Sep. 27, 2018]. Retrieved from the Internet <URL: http://www.podiatryinstitute.com/pdfs/update_1993/1993_28.pdf>.*

Coughlin, Michael, Common Causes of Pain in the Forefoot in Adults, (Aug. 2000), The Journal of Bone and Joint Surgery,vol. 82-B, No. 6, pp. 781-790 (Year: 2000).*

"Phenol," HPA Compendium of Chemical Hazards, 2011, Version 4, 32 pages.

Chapeskie, "Ingrown Toenail or overgrown toe skin?" Canadian Family Physician, 2008, vol. 54, No. 11, pp. 1561-1562.

Choi et al. "Short-Term Heat Exposure Inhibits Inflammation by Abrogating Recruitment of and Nuclear Factor-κB Activation in Neutrophils Exposed to Chemotactic Cytokines." The American Journal of Pathology, 2008, vol. 172(2), pp. 367-377.

Clayton et al., Patty's Industrial Hygiene and Toxicology, 3rd Edition, J Wiley and Sons, New York, 1982, p. 2583.

De Pomerai et al. "Growth and maturation of the nematode Caenorhabditis elegans following exposure to weak microwave fields." Enzyme and Microbial Technology, 2002, vol. 30(1), pp. 73-79.

Fausch et al. "Human Papillomavirus Can Escape Immune Recognition through Langerhans Cell Phosphoinositide 3-Kinase Activation." The Journal of Immunology, 2005, vol. 174(11), pp. 7172-7178.

Gao et al. "Non-ablative controlled local hyperthermia for common warts." Chinese Medical Journal, 2009, vol. 122(17), pp. 2061-2063.

U.S. Appl. No. 13/483,266, filed May 30, 2012 now U.S. Pat. No. 9,498,284.

U.S. Appl. No. 15/251,113, filed Aug. 30, 2016

U.S. Appl. No. 15/938,238, filed Mar. 28, 2018

U.S. Appl. No. 16/869,886, filed May 8, 2020.

U.S. Appl. No. 13/183,759, filed Jul. 15, 2011 now U.S. Pat. No. 9,662,510.

U.S. Appl. No. 15/213,946, filed Jul. 19, 2016.

U.S. Appl. No. 16/277,146, filed Feb. 15, 2019.

U.S. Appl. No. 16/277,171, filed Feb. 15, 2019.

Hong-Xia et al. "Detection with the Polymerase Chain Reaction of Human Papillomavirus DNA in Condylomata Acuminata Treated with CO2 Laser and Microwave," International Journal of Dermatology, Mar. 1995, vol. 34, No. 3, pp. 209-211.

Kashima et al. "Polymerase chain reaction identification of human papillomavirus DNA in CO2 laser plume from recurrent respiratory papillomatosis." Otolaryngology Head Neck Surgery, 1991, vol. 104(2), pp. 191-195.

Li et al. "Detection with the Polymerase Chain Reaction of Human Papillomavirus DNA in Condylomata Acuminata Treated with CO2 laser and Microwave." International Journal of Dermatology, 1995, vol. 34(3), pp. 209-211.

Lipke "An Armamentarium of Wart Treatments," Clinical Medicine & Research, 2006, vol. 4(4), pp. 273-293.

Ogura et al."Microwave hyperthermia treatment increases heat shock proteins in human skeletal muscle," British Journal of Sports Medicine, 2007, vol. 41, pp. 453-455.

Parker et al. "Specifying a Ferrite for EMI Suppression," Conformity, Jun. 2008, pp. 50-59.

Skitzki et al. "Hyperthermia as an immunotherapy strategy for cancer." Current Opinion in Investigational Drugs, Jun. 2009, vol. 10(6), pp. 550-558.

Smith et al. "Microwave thermal balloon angioplasty in the normal rabbit," American Heart Journal, Jun. 1992, vol. 123, No. 6, pp. 1516-1521.

Tonomura et al. "Effects of Heat Stimulation via Microwave Applicator on Cartilage Matrix Gene and HSP70 Expression in the Rabbit Knee Joint." Journal of Orthopaedic Research, 2008, vol. 26(1), pp. 34-41.

* cited by examiner

METHOD AND APPARATUS FOR THE TREATMENT, MANAGEMENT AND/OR CONTROL OF PAIN

FIELD OF THE INVENTION

The present invention provides methods and apparatus for the treatment, management and/or control of pain, in particular pain associated with or caused or contributed to by certain dermatological conditions.

BACKGROUND OF THE INVENTION

Pain takes many different forms and is often associated with disease; indeed pain can be a major symptom of certain diseases and/or conditions. The mechanisms and pathologies which underpin each type of disease can vary dramatically depending often on the duration, location and nature of the disease itself. As a consequence achieving effective and permanent pain relief/management can be time consuming, problematic and complex.

Many diseases and/or conditions result in pain. Sometimes that pain is local and sometimes it is more widespread and felt throughout the body. The pain may be constant or intermittent with a sharp or throbbing sensation.

Dermatologic disease can have a cancerous, bacterial, fungal and/or viral aetiology and symptoms often include the presence of painful lesions. These lesions may take the form of blisters, sores, corns, warts and/or calluses and are often (but not always) present on the plantar regions of the feet and or the hands (including palms). Further, and depending on the nature or location of the dermatological disease and/or condition, the pain associated with these lesions may be acute or chronic and/or local (to the lesion) or more wide-spread.

In some cases, while the disease, condition and/or any associated lesion may itself not be problematic, the pain may be sufficiently troublesome, that some form of pain relief is required.

Drugs can be used to manage pain and there are a number of prescription and/or over-the-counter remedies available for use. However, continual and/or regular use of such drugs is not ideal and can lead to other health problems, overdose and/or addiction.

In some cases, the only form of effective and permanent pain relief may be via treatment of the disease itself or the surgical removal of any lesion which is causing pain. However, surgery carries with it a significant risk of further damage/injury, infection and pain—not to mention prolonged recovery periods and procedures that do not properly cure the problem.

As such there is a need for new methods which can relieve the pain, including the pain that is associated with and/or caused or contributed to by a range of dermatological conditions.

SUMMARY OF THE INVENTION

The present invention is based on the finding that microwave energy may be used in the treatment, prevention and/or management of pain. Specifically, it has been shown that pain associated with some ailments, including for example certain dermatological diseases and/or conditions can be at least partially relieved by the application or administration of microwave energy.

As such, this disclosure provides a method for treating, preventing and/or managing pain in a subject, said method comprising administering microwave energy to a subject in need thereof.

Additionally, there is provided the use of microwave energy and/or an apparatus or device capable of emitting or generating the same, for treating, preventing and/or managing pain. Further, this disclosure provides microwave energy and/or an apparatus or device capable of emitting or generating microwave energy, for use in treating, preventing and/or managing pain.

It should be noted that the methods described herein may require the use of a pain "treating, preventing and/or managing amount" of microwave energy. Such an amount may otherwise be referred to as a "therapeutic", "analgesic" or "pain relieving" amount of microwave energy. Suitable therapeutic, analgesic and/or pain relieving forms and/or amounts of microwave energy are disclosed herein.

A particular application of the disclosed microwave energy is the treatment of pain that is associated with or caused or contributed to by one or more dermatological diseases and/or conditions. As such, this disclosure provides a method for treating, preventing and/or managing pain associated with or caused or contributed to by one or more dermatological diseases and/or conditions, said method comprising administering a subject experiencing pain associated with or caused or contributed to by one or more dermatological diseases and/or conditions, one or more doses of microwave energy.

Additionally, there is provided the use of microwave energy and/or an apparatus or device capable of emitting or generating the same, for treating, preventing and/or managing pain associated with or caused or contributed to by one or more dermatological diseases and/or conditions. Further, this disclosure provides microwave energy and/or an apparatus or device capable of emitting or generating microwave energy, for use in treating, preventing or managing pain associated with or caused or contributed to by one or more dermatological diseases and/or conditions.

A dermatological disease and/or condition may be defined as any disease or condition of or effecting the skin and/or its various layers (the epidermis (which includes the stratum corneum, stratum lucidum, stratum *granulosum*, stratum *spinosum* and stratum germinativum (or stratum basale), the dermis, papillary region, reticular region), structures (including hairs, nails, receptors, hair follicles, sweat glands, sebaceous glands, pores, apocrine glands, lymphatic vessels, blood vessels and the like) and/or tissues.

The various layers, structures and/or tissues of the skin may be collectively defined as skin "components" and as such, the term dermatological diseases and/or conditions may relate to diseases and/or conditions effecting one or more components of the skin. The term "skin" may include any region of the skin of a human or animal subject and may further include the mucosal surfaces, membranes and/or tissues. For example, the term "skin" may embrace skin or tissue present on or within the female/male reproductive systems (including genitals), the respiratory system, the head, the neck, the thorax, the abdomen, the anal/rectal regions, arms, hands, palms, legs feet, plantar and/or oral locations.

Thus, the term "pain" may relate to pain in the skin and/or one or more components thereof and/or pain which is associated with and/or caused or contributed to by one or more dermatological conditions.

As such, the term "dermatological diseases and/or conditions" shall be taken to embrace all diseases of the skin (but perhaps also the nails and/or hair) which result in, cause or are associated with pain. The term "dermatological diseases and/or conditions" may embrace those diseases and/or conditions having a genetic, allergic, autoimmune, cancerous (malignant), viral, fungal and/or bacterial (or "microbial") aetiology and may embrace "lesions" including, for example, tumours, warts, corns (of all types), calluses, keratin disorders and the like. As such, the phrase "dermatological disease and/or condition" embraces virus associated diseases and/or conditions including those caused or contributed to by human papilloma virus (HPV). The term further embraces those diseases and/or conditions referred to as neurovascular corns, intractable plantar keratosis, (characterised by discrete, focused calluses) and porokeratosis (including all and any of its variations).

A "subject in need thereof" may be any human or animal subject experiencing pain or predisposed/susceptible to pain or any human or animal subject experiencing pain which is associated with or caused or contributed to by a dermatological disease and/or condition. The subject (or "subject in need thereof") may be suffering from (or predisposed/susceptible to) one or more dermatological conditions which are known to result in pain.

Pain which is treatable by the methods, uses and/or apparatus described herein may be acute or chronic and may be experienced or felt throughout the body or in one or more specific regions or tissues. For example, the pain may be a general pain which is wide-spread and felt or experienced throughout the body. The pain may be a local pain—that is pain localised or confined to a specific region or tissue of the human or animal body. For example (and in the context of skin pain or pain which is associated with or caused or contributed to by one or more dermatological diseases and/or conditions) the pain may be local and confined to and/or experienced or felt within or proximal to the tissues or parts of the skin affected by a dermatological disease and/or condition and/or local to one or more skin lesion(s), corn(s), callous(es) and/or wart(s).

The microwave energy based methods (and apparatus and/or devices for generating the same described herein) may be used to treat, prevent or manage pain of all types including, for example, nociceptive pain, neuropathic pain, inflammatory pain, pain associated with disease (for example cancer pain) and the like.

In terms of "managing", "treating", "controlling" and/or "preventing" pain (including pain caused or contributed to by a dermatological disease and/or condition), the microwave energy may be used to achieve partial and/or complete pain relief in a subject. Microwave energy may also be exploited in order to achieve and/or induce a state of (at least local) analgesia in a subject. The state of local analgesia may be confined to, for example the skin, a component thereof and/or any lesion, corn, callous and/or wart thereof.

The inventors have noted that microwave energy may be used to relieve the pain associated with, for example, HPV associated lesions (verrucas for example) and corns. A corn may be described as a painful callus of dead skin. There are many different types of corn and pain associated with any of these may be relieved (treated, prevented and/or managed) by application of microwave energy as described herein. While most corns comprise only dead tissue, neurovascular corns contain nerves and blood vessels. This not only makes them difficult to treat and/or resolve but they are sensitive and often extremely painful. Treatment usually involves removal under local anaesthetic but this can lead to further pain and bleeding. Despite often extensive lesion/tissue excision and application of caustic agents to destroy existing corn tissue, they can re-occur and further treatment is needed. Advantageously, microwave energy may be used to relieve, treat, prevent and/or manage pain associated with corns and in particular neurovascular corns.

As such, this disclosure provides a method of managing, treating and/or preventing pain associated with and/or caused or contributed to by one or more corn(s) in a subject, said method comprising administering microwave energy to a subject.

The subject may be any subject suffering from pain associated with a corn. The subject may be any subject predisposed and/or susceptible to developing a corn, in particular, painful corns. The amount of microwave energy administered to said subject may be an amount effective to achieve at least partial relief from the pain associated with the corn.

The corn may be a neurovascular corn.

The subject may have a plurality of corns.

Additionally, because HPV associated diseases and/or lesions (including verrucas) can be painful, the microwave energy based methods described herein may be used to relieve the pain associated therewith. The methods described herein may further be used to treat, prevent, manage and/or relieve pain associated with verrucas.

The methods described herein may also be applied to the treatment, management, relief and/or prevention of pain associated with, intractable plantar keratosis and porokeratosis (including all and any of its variations).

In all cases, the microwave energy may be applied prophylactically in order to prevent pain or to prevent dermatological conditions of the type described herein from becoming painful.

The methods described herein may involve the application of one or more microwave energy doses to the site or sites of the pain and/or the dermatological disease and/or condition which is causing pain. For example, the methods may involve the application of one or more microwave energy doses directly to a skin lesion. By way of further example, where the disease or condition is characterised by the presence of corns (for example neurovascular corns), the microwave energy may be applied directly to each corn and/or generally to a region or area of the skin containing the corn(s).

The subject may be any subject experiencing pain, in particular, pain occurring as a consequence of a disease and/or condition. The disease and/or condition may be any of those described herein, including, for example diseases and/or conditions caused or contributed to by human papilloma virus (HPV), malignant conditions (including those with an HPV aetiology) and/or a range of dermatological conditions including those in which tissue (for example skin) is infected with one or more microbial (for example viral) pathogen(s). The pain to be treated, managed or prevented may be pain associated with a lesion—for example a lesion with HPV aetiology. The pain may be pain associated with a wart. In such cases, microwave energy may be used to reduce the pain associated with the lesion and thus the pain experienced by the subject.

The pain may become treated or managed (altered, improved or resolved) prior to the resolution of the disease, condition or lesion which is inducing or causing the pain. For example a subject may be subjected to a microwave based treatment to achieve the resolution of the relevant disease/condition or lesion and, prior to effective resolution, any pain associated with the disease, condition or lesion, is (or becomes) managed and/or treated. Microwave energy as described herein may affect complete or partial pain relief within one or two treatment doses whereas treatment (or resolution) of the disease, condition or lesion itself may take more doses.

In view of the above, the microwave energy based method of treating or preventing pain disclosed herein may be used concurrently or simultaneously with any of the microwave energy based methods of treating or preventing diseases or conditions described herein.

Microwave energy useful in the treatment, prevention or management of pain may have a frequency of between about 500 MHz and about 200 GHz. In other embodiments, the frequency of the microwave energy may range from between about 900 MHz and about 100 GHz. In particular, the frequency of the microwave energy may range from about 5 GHz to about 15 GHz and in a specific embodiment has a frequency of 8 GHz. Depending on the nature or type of disease and/or condition causing the pain which is to be treated, prevented or managed, a certain degree of microwave energy penetration through the skin may be required. One of skill will appreciate that higher frequency microwave energy may not penetrate as far as lower frequency microwave energy. For example, where the microwave energy is required to penetrate the skin to a depth of a few millimetres (mm) a frequency in the range of, for example, 5.8 GHz to 15 GHz may be used—again, and without wishing to be bound by theory, this frequency range may be preferable because higher frequency microwave energy may not penetrate sufficiently. The power level and energy density of the application or dose will also affect the depth of penetration therefore lower frequencies may be used with appropriately designed applicators and treatment profiles.

It should be understood that the methods of treatment described herein may require the use of microwave energy having a single frequency or microwave energy across a range of frequencies. For example a method of use of this disclosure may require that the subject be administered two or more doses of microwave energy, each dose comprising a specific frequency of microwave energy which frequency is different to or the same as the frequency of microwave energy used (or to be used) in any preceding or subsequent dose. In any given dose, the frequency of microwave energy used may be variable in that it modulates within a given frequency range.

It is known that microwave energy may be used in the treatment and/or prevention of certain dermatological conditions (including, for example, those caused or contributed to by human papilloma virus) and that is can raise and/or modulate a host immune response. However, the microwave energy used in the pain relieving methods and uses of this disclosure may be applied at a level which is sub-curative. A sub-curative amount of microwave energy may not act to resolve the dermatological disease or condition itself, rather the microwave energy and/or any administered microwave energy based protocol may be effective only to achieve a degree of (for example, local) pain relief as described herein.

The microwave energy may be used so that it exposes the subject to a level of microwave energy of anywhere between about 1 J and about 500 J, for example, about 5 J to about 200 J. The microwave energy for use in a method of stimulating an immune response in a subject may be used at about 5 J, about 10 J, about 50 J, about 100 J or about 200 J.

The microwave energy may be applied for any suitable duration of time. The microwave energy may be applied for anywhere between about 0.1 s and about 1 minute. The microwave energy may be applied for about 1 s, about 5 s about 10 s, about 20 s or about 30 s. The microwave energy may be applied as multiple bursts or pulses of the same or different duration and/or of (or at) the same or different frequency/energy level. Each applied microwave energy burst/pulse may last for the same or a different duration. As stated, an applied amount of microwave energy may be described as a "microwave energy dose"

A subject may be delivered one or more microwave energy doses over a predetermined period of time. For example, a subject may be administered a single dose on 1 day or multiple doses over the same day, each dose being separated by a non-dosing period. Additionally or alternatively, a subject may be administered other doses on subsequent days. A treatment (comprising one or more microwave energy doses) may last a day, multiple days or one or more weeks months or years.

Where pain results from a small dermatological lesion (corn, wart or the like), a single dose may be applied to a single site within, on or to, the lesion. A small lesion (for example a small corn, callus or verruca) may be one which is up to about 7 mm in diameter. Where the pain results from a lesion which is larger, for example larger than about 7 mm, the lesion (for example corn, callus or verucca) may be applied multiple doses in a manner that ensures that the entire surface or area of the lesion has been exposed to microwave energy. One of skill will appreciate that the number of doses required to achieve pain relief and/or to treat or prevent pain associated with or caused or contributed to by a dermatological condition may vary and a number of factors including, for example, the severity of the pain, the size of the lesion (wart, corn or the like) and/or its depth of skin penetration, the location and spread of the lesion (wart, corn or the like) must be taken into consideration when determining how many doses to administer a subject. In some cases the number of doses required may be any number required to achieve pain relief in a subject.

As stated, each microwave energy dose may be applied directly to the source of the pain (for example the site of a lesion, wart or corn) and/or to a region which is proximal to the source of the pain.

Accordingly, disclosed herein is an apparatus for use in treating, preventing and/or managing pain, in particular pain associated with and/or caused or contributed to by any of the dermatological conditions and/or diseases described herein, said apparatus comprising a microwave source for providing microwave energy and means for administering or delivering the microwave energy to a subject (and/or pain site thereof) to be treated. The apparatus provided by this aspect of the invention may be used in any of the methods and uses described herein.

The apparatus may further comprise means for controlling at least one property of the microwave energy produced by the microwave source. For example the means may control or modulate the duration, power, frequency, wavelength and/or amplitude of the microwave energy. The means for controlling the microwave energy may be integral with the apparatus or separately formed and connectable thereto.

In one embodiment, the microwave energy source may produce microwave energy at a single frequency and/or microwave energy across a range of frequencies. The means for controlling at least one property of the microwave energy may permit the user to select or set a particular microwave or microwaves to be produced by the apparatus and/or the properties of the microwave(s) produced.

The apparatus may further comprise means for monitoring the microwave energy produced or generated by the microwave source. For example, the apparatus may include a display indicating one or more properties of the microwave energy. The apparatus may be programmable in that it can be set to deliver one or more predetermined microwave energy doses to a subject.

In one embodiment, the means for administering or delivering the microwave energy to a subject to be treated comprises an applicator formed, adapted and/or configured to deliver or administer microwave energy to the subject. The inventor has discovered that the dielectric properties of tissue affected by a dermatological disease and/or condition vary with respect to normal, healthy, tissue (i.e. tissue not affected by a dermatological disease and/or condition). As such, the means for delivering microwave energy may electrically match the range of epsilon relative values of the tissue affected by a dermatological disease and/or condition. In this way, it is possible to ensure efficient delivery of the microwave energy to the tissue.

Advantageously, the means for delivering the microwave energy to a subject may comprise a component or part for contact with a subject to be treated. The part or component for contact with the subjected to be treated may be removable such that it can be discarded or sterilised after use. In one embodiment, the means for delivering the microwave energy may comprise a single application element or a hand piece which accepts a removable tip which can either be a single use, disposable component or a reusable component intended to be sterilized between uses. Advantageously, the part or component for contact with the subject to be treated may comprise a reuse mitigation function to prevent accidental or attempted reuse.

In one embodiment, the part or component for contact with the subjected to be treated may be shaped, formed or adapted so as to be compatible with a particular internal or external body part, surface or lesion thereof. For example, the part or component may comprise a domed, curved or enclosing surface, compatible with the physical properties or profile of an internal or external body part, a surface or a lesion thereof, including, for example a corn (including a neurovascular corn) or a papilloma such as a wart or verucca.

The means for delivering the microwave energy to a subject may be connected to the microwave source via a flexible cable. In one embodiment the means for delivering the microwave energy to a subject (i.e. the applicator) may be connected to the microwave source via a flexible cable with locking connections having both microwave and signal data cables and may be reversible to enable connection to either port.

In one embodiment the invention provides an apparatus for delivering microwave energy to infected tissue the apparatus comprising:—a microwave source for providing microwave energy, connectable to a system controller for controlling at least one property of the microwave radiation provided by the microwave source; and a monitoring system for monitoring the delivery of energy and an applicator means, for example an applicator device, for delivering microwave energy, wherein:—the applicator is configured to deliver precise amounts of microwave energy provided by the source at a single frequency or across a range of frequencies.

DETAILED DESCRIPTION

Figure 1B:
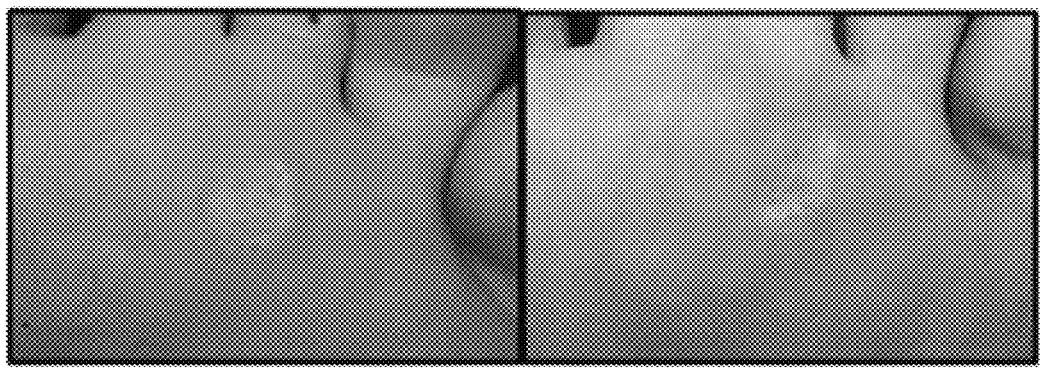
Figure 1C:
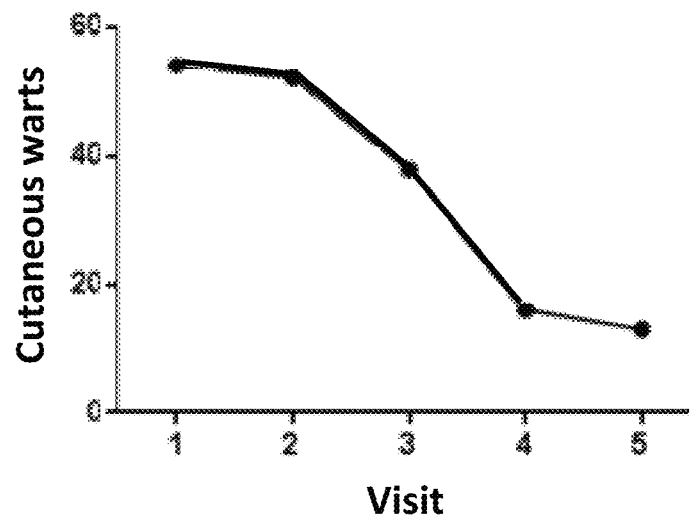
Figure 1D:
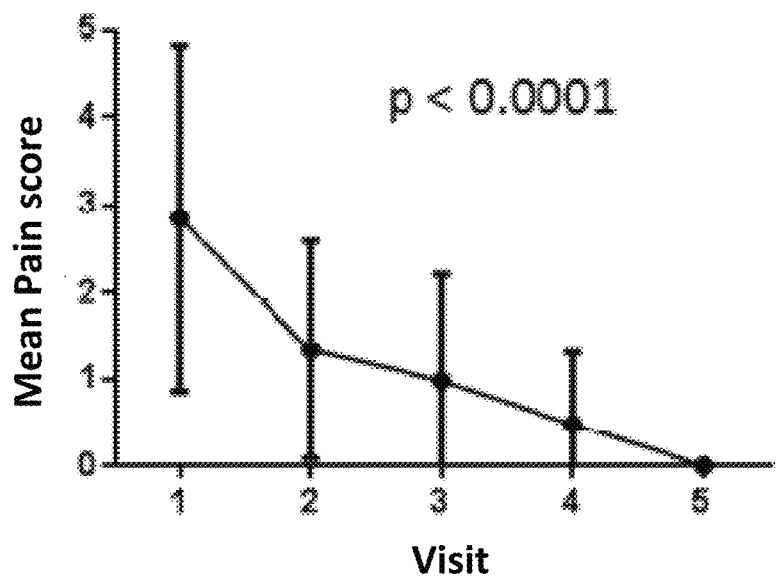

The present invention will now be described in detail by reference to the following Figures which show:
FIG. 1A: Clinical image of plantar wart pre-microwave treatment (left), after one treatment (middle) and after two treatments (right). FIG. 1B. Clinical image of plantar wart pre-microwave treatment (left), after one treatment (right). FIG. 1C. Intention to treat analysis of 32 patients with 54 HPV foot warts were treated by microwave therapy over 5 visits: baseline, 1 week, 1 month, 3 months, and 12 months. Resolved warts were enumerated. FIG. 1D. Pain scores were assessed using a 10 point visual analogue score at each visit. Statistical test: One-way ANOVA.

EXAMPLE 1

Methods and Materials
Patients and In Vivo Microwave Treatment
Patients with treatment-refractory plantar warts were excluded if they had a pacemaker fitted, were pregnant or breast feeding, had any metal implants within the foot or ankle, suffered any known disease or condition affecting their immune function or their capacity to heal. Adverse events were categorized as being specifically associated with the microwave procedure, or unrelated. A complete examination of the affected area was undertaken at each study visit. In addition, quantitative measures of pain and neuromuscular function were assessed by the physician. At the conclusion of the treatment session all patients were given an advice information sheet advised to report any complications. No post-operative dressing was required and patients were advised to subsequently undertake normal everyday activities as usual with no restrictions.

A total of 32 patients with 54 foot warts were enrolled into the study. Of the 32, 17 were males and 15 females. Ages ranged from 22-71 years with a mean age of 44.79 years (sd 13.019]. Of the 54 lesions, 16 were reported as single lesions, and 38 as multiple type lesions (including mosaic verrucae). The average lesion duration was 63 months (5.25 years) with a range of 2-252 months (<1-21 years). The mean lesion diameter was 7.43 mm (sd 6.021), ranging from just 2 mm to 38 mm in diameter.

The procedure was performed in an out-patient setting, with standard podiatric facilities. The Swift device settings were titrated up as tolerated to 50 J over a 7 mm2 application area (7.14 j/mm2). The microwave energy was delivered to the affected area over 5 s duration (50 J delivered as 10 watts for 5 s). Lesions which were <7 mm in diameter were treated with one application of the probe at a single treatment session whilst lesions >7 mm were underwent multiple applications until the entire surface of the wart had been treated.

Clinical assessments were performed at baseline and at 1 week, 1 month, 3 months, and 12 months after treatment by a podiatrist experienced in the management of plantar warts. Response to treatment was assessed by the same investigator as 'completely resolved' or 'unresolved'. Complete resolution was indicated by fulfilling three criteria: i. lesion no longer visible, ii. return of dermatoglyphics to the affected area, iii. no pain on lateral compression. Pain was assessed using a 10 point visual analogue scale.
Human Skin and Ex Vivo Microwave Treatment
Normal skin samples were acquired from healthy individuals after obtaining informed written consent with approval by the Southampton and South West Hampshire Research Ethics Committee in adherence to Helsinki Guidelines. Skin samples were treated immediately ex-vivo with microwave (Swift s800; Emblation Ltd., UK) or liquid nitrogen therapy and treated skin excised. Excised skin was sent for histological analysis or placed in culture media. Histological analysis with hematoxylin and eosin (H&E) tissue sections were undertaken following fixation and embedded in paraffin wax. DNA damage was assessed by staining for single stranded and double stranded DNA breaks by TUNEL assay using the ApopTag® In Situ Apoptosis Detection Kit (Millipore, UK). Following culture, supernatants were collected and analysed for lactate dehydrogenase release using the Cytotoxicity Detection Kit (Roche applied science) as a measure of apoptosis.

Reductions in pain were observed as treatment progressed (FIG. 1D). Statistically significant reductions were observed in mean pain scores between each treatment appointment (p<0.0001) to resolution. Adverse events were minimal. One patient reported prolonged pain from the treatment which required a simple oral analgesic (paracetamol) but the pain subsided within 24 hours. This individual withdrew from the study. No further adverse events were reported. No cases of scarring were recorded following completion of treatment. No cases of neuromuscular dysfunction were reported.

Culture and In Vitro Microwave Treatment.

Human skin and HaCaT keratinocytes were cultured in calcium-free DMEM (ThermoFisher Scientific) with 100 U/mL penicillin, 100 µg/mL streptomycin, 1 mM sodium pyruvate, 10% fetal bovine serum (FBS) and supplemented with calcium chloride at 70 µM final concentration. Lymphocytes were cultured in RPMI-1640 media with 100 U/mL penicillin, 100 µg/mL streptomycin, 1 mM sodium pyruvate, 292 µg/mL L-glutamine, supplemented with 10% FBS or 10% heat inactivated human serum (HS). HaCaT cells were cultured at sub-confluency to avoid cell differentiation and used in assays at passage 60-70. Cells were plated at 2.5×103 cells/well in 96-well flat plate (Corning Costar) and cultured overnight to reach confluence. HaCaTs were washed once with PBS before treatment with 150 J microwave, liquid nitrogen (10 s), heat (42° C. preheated media) or with LPS+IFN-γ (1 ng/mL+1000 U/mL). Cells were cultured for 24 h before supernatants were harvested.

For HPV-specific T cell lines, PBMCs were isolated from HLA-A2 individuals as previously described 11. PBMCs were seeded at 2-4×106 cells/well in 24-well culture plate and 10 µg/mL of 9mer HLA-A2 restricted HPV16 epitope LLM (LLMGTLGIV) 12 was added, cells were cultured in 1 mL RPMI+10% HS. On day 3, cells were fed with RPMI+10% HS+IL-2 (200 IU/mL), and then fed again on day 7 or when needed. After day 10, HPV-specific T cells were harvested for cryopreservation before testing against HPV in ELISpot assays.

Monocyte derived dendritic cells (moDCs), CD14+ cells were positively isolated from PBMCs by magnetic separation using CD14 microbeads (Milentyi Biotec), according to manufacturer's protocol.

Cells were washed and resuspended in RPMI+10% FBS+ 250 U/mL IL-4 and 500 U/mL GM-CSF. At day 3, cells were fed with RPMI+10% FBS+IL-4 and GM-CSF, and then harvested on day 5 for use in functional assays.

In vitro, microwave therapy of cell cultures was delivered through the base of the plastic culture dish and showed a linear dose response between the energy delivered and thermal induction (not shown). Utilising the equation $E=m \times c \times \theta$ (E=energy transferred, J; m=mass, kg; c=specific heat capacity, J/kg ° C.; θ=temperature change, ° C.), we calculated that in our system the 150 J Swift programme delivered 15.58 J (s.d. 0.921) through the plastic to the culture.

ELISpot, Flow Cytometry and qPCR

Keratinocytes were treated with microwave at various energy settings before removal of supernatant at various time points. MoDCs were treated overnight with keratinocyte supernatant, then washed twice before incubation with 10 µg/mL LLM peptide for 2 hours before a further wash.

Human IFN-γ ELISpot (Mabtech, Sweden) was undertaken as per manufacturer's protocol and as reported previously 11.1×103 moDCs were plated with autologous HPV peptide-specific T cells at 1:25 ratio. Spot forming units (sfu) were enumerated with ELISpot 3.5 reader (AID, Germany). MoDCs were treated with HaCaT supernatant and harvested at 24 hours for flow cytometric analysis of cell phenotype. Cells were stained with violet LIVE/DEAD stain (Invitrogen) for 30 min at 4° C., then washed with PBS+1% BSA and stained with antibodies PerCP-Cy5.5 anti-HLA-DR, FITC anti-CD80, FITC anti-CD86, PE anti-CD40, all purchased from BD, for 45 min at 4° C. Cells were washed then resuspended in PBS+1% BSA and analysed using the BD FACSAria and the FlowJo v10.0.08 analysis software. The expression of chosen genes was validated with quantitative PCR, using the TaqMan gene expression assays for target genes: YWHAZ (HS03044281_g1), IRF1 (Hs00971960_m1), IRF4 (Hs00543439_CE) (Applied Biosystems, Life Technologies, Paisley, UK) in human skin treated as indicated. RNA extraction (RNeasy micro kit, Qiagen) and reverse transcription (NanoScript kit; Primer Design, Southampton, UK) were carried out accordingly to the manufacturer's protocol.

Results

Reductions in pain were observed as treatment progressed (FIG. 1D). Statistically significant reductions were observed in mean pain scores between each treatment appointment (p<0.0001) to resolution. Adverse events were minimal. One patient reported prolonged pain from the treatment which required a simple oral analgesic (paracetamol) but the pain subsided within 24 hours. This individual withdrew from the study. No further adverse events were reported. No cases of scarring were recorded following completion of treatment. No cases of neuromuscular dysfunction were reported.

EXAMPLE 2

This Example relates to the use of microwave energy to achieve pain relief in a long term sufferer of neurovascular corns.

Neurovascular corns are vascularised dermal tissue which penetrate into the epidermis. Not only does this make them very hard to treat but it means that they are frequently characterised by extensive vascularisation and a well-developed nerve supply. This renders them painful. While they can occur on the foot where there is increased pressure or friction, they are more common in those that smoke. The subject detailed below was a smoker, consuming in the region of 10 cigarettes a day.

Case Study Details

Subject: A 60 year old male patient

Lesion: neurovascluar corn

History: 8-10 years in duration

Current status: 5 mm in circumference

Treatment: debridement and 5 watts applied for 5 seconds

Result: Subject reported an immediate reduction in pain post treatment.

Discussion: The reduction in pain was unexpected, especially for this condition (neurovascular corns).

The invention claimed is:

1. A method for treating pain in a subject, said method comprising:
    administering microwave energy to said subject, wherein the pain is caused by or associated with a dermatological disease and/or condition and the microwave energy is administered at a level which is sub-curative to the dermatological disease and/or condition, the dermatological disease and/or condition consisting of at least one of a wart, a tumor, a papilloma infection, an HPV associated/positive cancer, a verruca, a corn, a callus, a neurovascular corn, an intractable plantar keratosis or a porokeratosis, and wherein the pain in the subject is reduced within one week after administering the microwave energy, wherein the microwave energy is administered at an energy of 50J and the microwave energy is delivered at 10 watts for a time of 5s.

2. The method of claim 1, wherein the administering includes repeated rounds of treatment with the microwave energy.

3. The method of claim 1, wherein the dermatological disease and/or condition has at least one of a microbial, genetic, allergic, autoimmune and/or malignant (cancerous) aetiology.

4. The method of claim 1, wherein the microwave energy is administered prophylactically.

5. The method of claim 1, wherein the microwave energy is administered directly to a site or cause of the pain.

6. The method of claim 1, wherein the microwave energy is administered at a frequency of at least one of:
between 500 MHz and 200 GHz;
between 900 MHz and 100 GHz; or
between 5 GHz to 15 GHz.

7. The method of claim 1, wherein the microwave energy has a frequency of 8 GHz.

8. The method of claim 1, wherein the microwave energy is administered as multiple bursts or pulses.

9. The method of claim 1, wherein the microwave energy is administered to the subject such that an entire surface that is affected by the dermatological disease and/or condition is exposed to the microwave energy.

10. A method for treating pain in a subject, wherein the pain is associated with or caused by at least one condition of:
a neurovascular corn;
intractable plantar keratosis; and
porokeratosis;
said method comprising:
administering microwave energy to said subject, wherein the microwave energy is administered at a level which is sub-curative to the at least one condition, and wherein the pain in the subject is reduced within one week after administering the microwave energy, wherein the microwave energy is administered at an energy of 50 J and the microwave energy is delivered at 10 watts for a time of 5s.

11. The method of claim 10, wherein the subject is administered one or more microwave energy doses.

12. A method for treating pain caused by or associated with a dermatological disease and/or condition in a subject, said method comprising:
administering microwave energy to said subject at a level which is sub-curative to the dermatological disease and/or condition, wherein the microwave energy is delivered using an apparatus comprising a microwave source and a delivery system for delivering the microwave energy to the subject, wherein the pain is caused by or associated with the dermatological disease and/or condition, the dermatological disease and/or condition consisting of at least one of a wart, a tumor, a papilloma infection, an HPV associated/positive cancer, a verruca, a corn, a callus, a neurovascular corn, an intractable plantar keratosis or porokeratosis, and wherein the pain in the subject is reduced within one week after administering the microwave energy, wherein the microwave energy is administered at an energy of 50J and the microwave energy is delivered at 10 watts for a time of 5s.

13. The method of claim 12, wherein the apparatus further comprises at least one of:
a controller for controlling at least one property of the microwave energy produced by the microwave source;
a monitor for monitoring the microwave energy produced by the microwave source.

14. The method of claim 12, wherein the delivery system for delivering the microwave energy electrically matches a range of epsilon relative values of tissue affected by at least one of the dermatological disease and/or condition.

15. The method of claim 12, wherein the delivery system for delivering the microwave energy to the subject comprises a component for contact with the subject.

16. The method of claim 15, wherein the component is removable such that it can be discarded or sterilised after use.

17. The method of claim 12, wherein the delivery system for delivering the microwave energy is compatible with at least one of:
an internal body part;
an external body part;
a bodily surface;
a lesion of an internal body part;
a lesion of an external body part; and
a lesion of a bodily surface.

18. The method of claim 12, wherein the apparatus is capable of administering microwave energy at a frequency of at least one of:
in a range of 500 MHz to 200 GHz;
in a range of 900 MHz to 100 GHz; or
in a range of 5 GHz to 15 GHz.

19. The method of claim 12, wherein the apparatus is capable of administering microwave energy at a frequency of 8 GHz.

20. The method of claim 12, wherein the microwave energy is administered as multiple bursts or pulses.

* * * * *